(12) United States Patent
Kane et al.

(10) Patent No.: US 10,179,237 B2
(45) Date of Patent: Jan. 15, 2019

(54) SYSTEMS AND METHODS FOR DETECTING DEVICE DISLODGMENT

(71) Applicant: Cardiac Pacemakers, Inc., St. Paul, MN (US)

(72) Inventors: Michael J. Kane, Roseville, MN (US); Allan Charles Shuros, St. Paul, MN (US); Brian L. Schmidt, White Bear Lake, MN (US); Keith R. Maile, New Brighton, MN (US); Benjamin J. Haasl, Forest Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 27 days.

(21) Appl. No.: 15/249,131

(22) Filed: Aug. 26, 2016

(65) Prior Publication Data

US 2017/0056649 A1 Mar. 2, 2017

Related U.S. Application Data

(60) Provisional application No. 62/211,418, filed on Aug. 28, 2015.

(51) Int. Cl.
*A61N 1/00* (2006.01)
*A61N 1/08* (2006.01)
(Continued)

(52) U.S. Cl.
CPC ............ *A61N 1/08* (2013.01); *A61N 1/36514* (2013.01); *A61N 1/36535* (2013.01);
(Continued)

(58) Field of Classification Search
CPC ............ A61N 1/36135; A61N 1/36535; A61N 1/36542; A61N 1/36578; A61N 1/3756; A61N 2001/083
See application file for complete search history.

(56) References Cited

U.S. PATENT DOCUMENTS 5,713,932 A 2/1998 Gillberg et al.
5,910,120 A 6/1999 Kim et al.
(Continued)

FOREIGN PATENT DOCUMENTS

EP 2760541 B1 5/2016
WO 2009039400 A1 3/2009

OTHER PUBLICATIONS

International Search Report and Written Opinion for Application No. PCT/US2016/049093, 21 pages, dated Dec. 5, 2016.

*Primary Examiner* — Scott Getzow
(74) *Attorney, Agent, or Firm* — Seager, Tufte & Wickhem LLP

(57) ABSTRACT

Systems, methods, and devices for detecting dislodgment of an implantable device are disclosed. In one example, a method for determining a dislodgement status may comprise collecting, by the implantable device operating in a first operating mode, a first number of accelerometer signal samples during a cardiac cycle of the heart and using the first number of accelerometer signal samples to determine a first patient parameter and collecting, by the implantable device operating in a second operating mode, a second number of accelerometer signal samples during a cardiac cycle of the heart and using the second number of accelerometer signal samples to determine a dislodgment status of the implantable device, wherein the first number is smaller than the second number. In some further embodiments, the method may further include providing a notification of the dislodgment status to a remote device that is remote from the implantable medical device.

18 Claims, 13 Drawing Sheets

(51) Int. Cl.
   *A61N 1/375*    (2006.01)
   *A61N 1/365*    (2006.01)
   *A61N 1/372*    (2006.01)
   *A61B 5/00*     (2006.01)

(52) U.S. Cl.
   CPC ..... *A61N 1/36542* (2013.01); *A61N 1/36585* (2013.01); *A61N 1/3756* (2013.01); *A61N 1/37252* (2013.01); *A61B 5/6869* (2013.01); *A61N 1/36578* (2013.01); *A61N 1/37205* (2013.01)

(56) References Cited

U.S. PATENT DOCUMENTS

| | | |
|---|---|---|
| 6,067,469 A | 5/2000 | Kim et al. |
| 6,195,584 B1 | 2/2001 | Hill et al. |
| 6,347,249 B1 | 2/2002 | Kim et al. |
| 6,484,050 B1 | 11/2002 | Carroll et al. |
| 6,490,486 B1 | 12/2002 | Bradley |
| 6,658,294 B1 | 12/2003 | Zadeh et al. |
| 6,807,439 B2 | 10/2004 | Edwards et al. |
| 7,286,875 B1 | 10/2007 | Park et al. |
| 7,873,410 B2 | 1/2011 | Cho et al. |
| 9,101,281 B2 | 8/2015 | Reinert et al. |
| 2012/0090627 A1 | 4/2012 | Ransbury et al. |
| 2012/0143278 A1 | 6/2012 | Ryu et al. |
| 2013/0079861 A1 | 3/2013 | Reinert et al. |
| 2013/0325081 A1 | 12/2013 | Karst et al. |
| 2013/0345536 A1 | 12/2013 | Doerr |

SYSTEMS AND METHODS FOR DETECTING DEVICE DISLODGMENT

CROSS REFERENCE TO RELATED APPLICATIONS

This application claims the benefit of U.S. Provisional Patent Application Ser. No. 62/211,418 filed on Aug. 28, 2015, the disclosure of which is incorporated herein by reference.

TECHNICAL FIELD

The present disclosure generally relates to systems, devices, and methods for detecting dislodgment of an implantable device, and more particularly, to systems, devices, and methods for detecting partial or full dislodgment of an implantable medical device from a heart wall.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, such devices may be attached, at least partially, to a wall of the heart by one or more fixation elements.

SUMMARY

The present disclosure generally relates to systems, devices, and methods for detecting dislodgment of an implantable medical device, and more particularly, to systems, devices, and methods for detecting partial or full dislodgment of an implantable medical device from a heart wall. In a first illustrative embodiment, a leadless cardiac pacemaker (LCP) may comprise a plurality of electrodes, an accelerometer, and a controller operatively coupled to the plurality of electrodes and the accelerometer. In some instances, the controller may be configured to collect, while in a first operating mode, a first number of accelerometer signal samples during a cardiac cycle of the heart and use the first number of accelerometer signal samples to determine a first patient parameter and collect, while in a second operating mode, a second number of accelerometer signal samples during a cardiac cycle of the heart and use the second number of accelerometer signal samples to determine a dislodgment status of the leadless cardiac pacemaker, wherein the first number is smaller than the second number. In at least some instances, the controller may be configured to provide a notification of the dislodgment status to a remote device that is remote from the leadless cardiac pacemaker.

Alternatively, or additionally, in any embodiments with respect to the first illustrative embodiment, the first patient parameter may be used by the LCP to affect a therapy delivered by the LCP.

Alternatively, or additionally, in any embodiments with respect to the first illustrative embodiment, the first patient parameter may comprise one of: a posture; and an activity level.

Alternatively, or additionally, in any embodiments with respect to the first illustrative embodiment, the first patient parameter may represent an activity level of the patient, and may be used by the LCP to affect a rate of delivery of pacing pulses to the plurality of electrodes.

Alternatively, or additionally, in any embodiments with respect to the first illustrative embodiment, the LCP may collect the accelerometer signal samples by selectively turning on and off the accelerometer.

Alternatively, or additionally, in any embodiments with respect to the first illustrative embodiment, the LCP may collect the first number of accelerometer signal samples during a first portion of the cardiac cycle and collects the second number of accelerometer signal samples during a second portion of the cardiac cycle.

Alternatively, or additionally, in any embodiments with respect to the first illustrative embodiment, the second portion of the cardiac cycle may include at least part of a polarization of the heart during the cardiac cycle, and the first portion of the cardiac cycle may begin after a repolarization of the heart during the cardiac cycle and ends before a subsequent polarization of the heart.

Alternatively, or additionally, in any embodiments with respect to the first illustrative embodiment, the first portion of the cardiac cycle may not include a contraction of a heart and the second portion of the cardiac cycle does include a contraction of the heart.

Alternatively, or additionally, in any embodiments with respect to the first illustrative embodiment, a beginning of the first portion of the cardiac cycle and a beginning of the second portion of the cardiac cycle may be offset by different amounts relative to a common detected feature of a sensed cardiac electrical signal.

Alternatively, or additionally, in any embodiments with respect to the first illustrative embodiment, the common detected feature of the sensed cardiac electrical signal may be an R-wave.

In a second illustrative embodiment, a method for determining a dislodgement status of an implantable device at an implant site on the heart of a patient, the implantable device having an accelerometer for providing an accelerometer signal, may comprise collecting, by the implantable device operating in a first operating mode, a first number of accelerometer signal samples during a cardiac cycle of the heart and using the first number of accelerometer signal samples to determine a first patient parameter and collecting, by the implantable device operating in a second operating mode, a second number of accelerometer signal samples during a cardiac cycle of the heart and using the second number of accelerometer signal samples to determine a dislodgment status of the implantable device, wherein the first number is smaller than the second number. In some embodiments, the method may further comprise providing a notification of the dislodgment status to a remote device that is remote from the implantable medical device.

Alternatively, or additionally, in any embodiments with respect to the second illustrative embodiment, the implantable device may be a leadless cardiac pacemaker.

Alternatively, or additionally, in any embodiments with respect to the second illustrative embodiment, the first patient parameter may be used by the implantable device to affect a therapy delivered by the implantable device.

Alternatively, or additionally, in any embodiments with respect to the second illustrative embodiment, the first patient parameter may comprise one of: a posture; and an activity level.

Alternatively, or additionally, in any embodiments with respect to the second illustrative embodiment, the first patient parameter may represent an activity level of the patient, and may be used by the implantable device to affect a pacing rate of a pacing therapy delivered by the implantable device to the heart of the patient.

Alternatively, or additionally, in any embodiments with respect to the second illustrative embodiment, the implantable may device collect the accelerometer signal samples by selectively turning on and off the accelerometer of the implantable device.

Alternatively, or additionally, in any embodiments with respect to the second illustrative embodiment, the implantable device may collect the first number of accelerometer signal samples during a first portion of the cardiac cycle and collects the second number of accelerometer signal samples during a second portion of the cardiac cycle.

Alternatively, or additionally, in any embodiments with respect to the second illustrative embodiment, the second portion of the cardiac cycle may include at least part of a polarization of the heart during the cardiac cycle, and the first portion of the cardiac cycle may begin after a repolarization of the heart during the cardiac cycle and ends before a subsequent polarization of the heart.

In a third illustrative embodiment, a leadless cardiac pacemaker (LCP) may comprise a plurality of electrodes, an accelerometer, and a controller operatively coupled to the plurality of electrodes and the accelerometer. In some embodiments, the controller may be configured to determine a patient parameter based at least in part on a first amount of accelerometer data collected during a cardiac cycle, determine a dislodgment status of the leadless cardiac pacemaker based at least in part on a second amount of accelerometer data collected during a cardiac cycle, wherein the first amount of accelerometer data is less than the second amount of accelerometer data, and communicate the dislodgment status to a remote device that is remote from the leadless cardiac pacemaker.

Alternatively, or additionally, in any embodiments with respect to the third illustrative embodiment, the first amount of accelerometer data and the second amount of accelerometer data may be collected during the same cardiac cycle.

Alternatively, or additionally, in any embodiments with respect to the third illustrative embodiment, the patient parameter may be used by the leadless cardiac pacemaker to affect a therapy delivered by the leadless cardiac pacemaker.

Alternatively, or additionally, in any embodiments with respect to the third illustrative embodiment, the patient parameter may comprises one of: a posture; and a patient activity level.

Alternatively, or additionally, in any embodiments with respect to the third illustrative embodiment, the first amount of accelerometer data may be collected during a first portion of the cardiac cycle and the second amount of accelerometer data is collected during a second portion of the cardiac cycle.

Alternatively, or additionally, in any embodiments with respect to the third illustrative embodiment, the first portion of the cardiac cycle may not include a contraction of a heart and the second portion of the cardiac cycle does include a contraction of the heart.

Alternatively, or additionally, in any embodiments with respect to the third illustrative embodiment, a beginning of the first portion of the cardiac cycle and a beginning of the second portion of the cardiac cycle may be offset by different amounts relative to a common detected R-wave.

In a fourth illustrative embodiment, a method may comprise detecting, by a leadless cardiac pacemaker (LCP) having an accelerometer, an occurrence of a cardiac electrical event, collecting, by the LCP operating in a first operating mode, accelerometer signal data during a first time period of a cardiac cycle, wherein the first time period begins a first predetermined amount of time after the detected cardiac electrical event, and collecting, by the LCP operating in a second operating mode, accelerometer signal data during a second time period of a cardiac cycle, wherein the second time period begins a second predetermined amount of time after the detected cardiac electrical event. In some embodiments, the method may further comprise determining, by the LCP, a dislodgment status of the LCP based at least in part on the accelerometer signal data collected during the second time period.

Alternatively, or additionally, in any embodiments with respect to the fourth illustrative embodiment, the cardiac electrical event may be an R-wave.

Alternatively, or additionally, in any embodiments with respect to the fourth illustrative embodiment, the first time period may begin between 300 ms and 800 ms after the detected R-wave.

Alternatively, or additionally, in any embodiments with respect to the fourth illustrative embodiment, the second time period may begin between 0 ms and 50 ms after the detected R-wave.

Alternatively, or additionally, in any embodiments with respect to the fourth illustrative embodiment, the first time period may not include a contraction of a heart and the second time period of the cardiac cycle does include the contraction of the heart.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
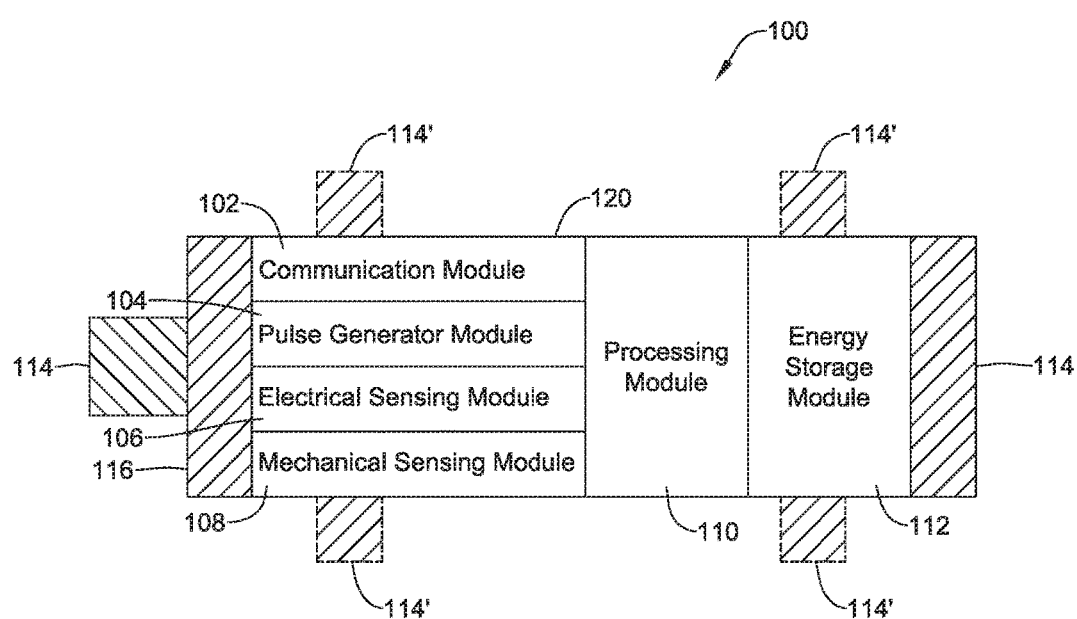
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for detecting device dislodgment from a heart. In some cases, devices of the present disclosure may be configured to implant on or within a heart of a patient. After implantation, the devices may become dislodged from the heart due to incorrect implantation or other reasons. This dislodgment may cause problems with the therapy delivered by the devices or the devices may migrate out of the heart and create a dangerous situation for the patient. This disclosure describes various devices, systems, and methods for detecting when a device becomes partially and/or fully dislodged from the heart.

FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may further include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100 and may, in some embodiments, be termed a controller. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias and other determinations such as whether LCP 100 has become dislodged. Processing module 110 may further receive information from communication module 102. In some embodiments, processing module 110 may additionally use such received information to determine occurrences and types of arrhythmias and/or and other determinations such as whether LCP 100 has become dislodged. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, processing module 110 may monitor one or more physiological parameters of the patient which may indicate a need for an increased heart rate (e.g. due to increased metabolic demand). Processing module 110 may then increase the rate at which pulse generator 104 generates electrical stimulation pulses.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In still other embodiments, processing module 110 may not be a single component. For example, processing module 110 may include multiple components positioned at disparate locations within LCP 100 in order to perform the various described functions. For example, certain functions may be performed in one component of processing module 110, while other functions are performed in a separate component of processing module 110.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy.

Figure 2:
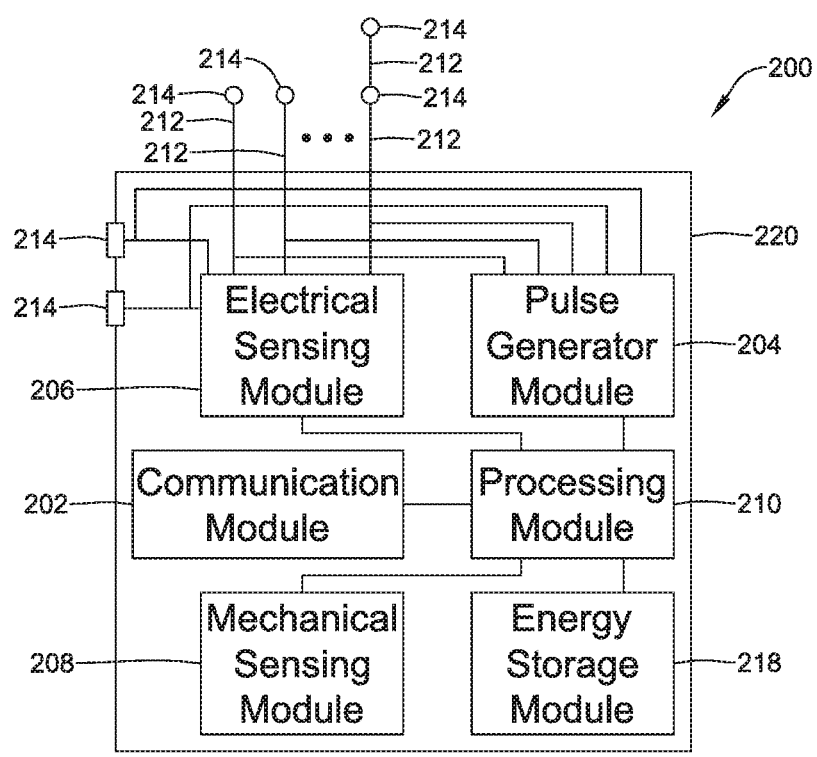
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, nerve stimulation/neuromodulation and/or other therapy types via leads 212 implanted within the heart.

In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
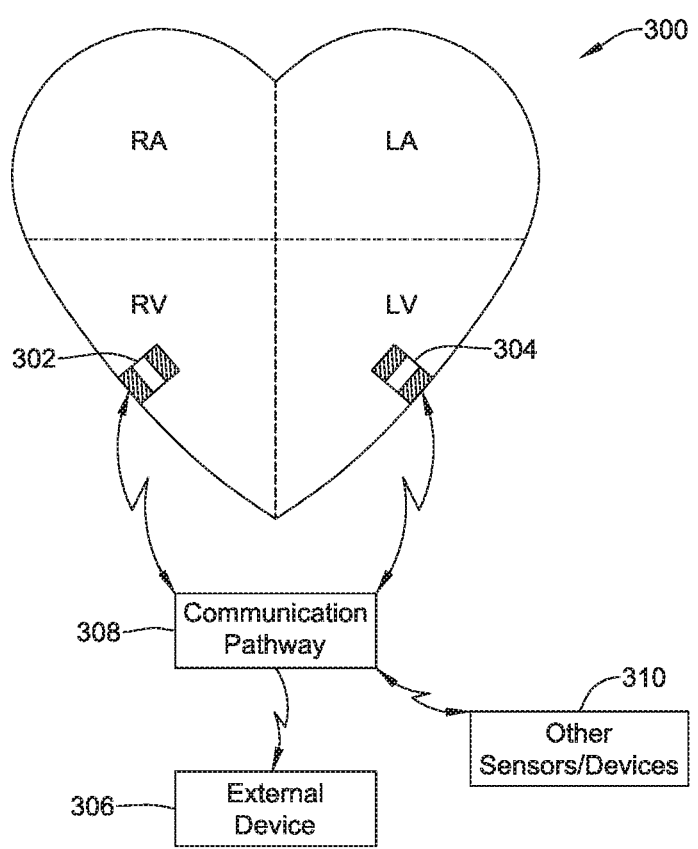
FIG. 3 is a schematic diagram of an exemplary medical system that includes multiple LCPs and/or other devices in communication with one another.

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. In at least some examples, external device 306 may represent an external support device such as a device programmer, as will be described in more detail below. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. a voltage and/or current waveform punctuated with current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Additionally, unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
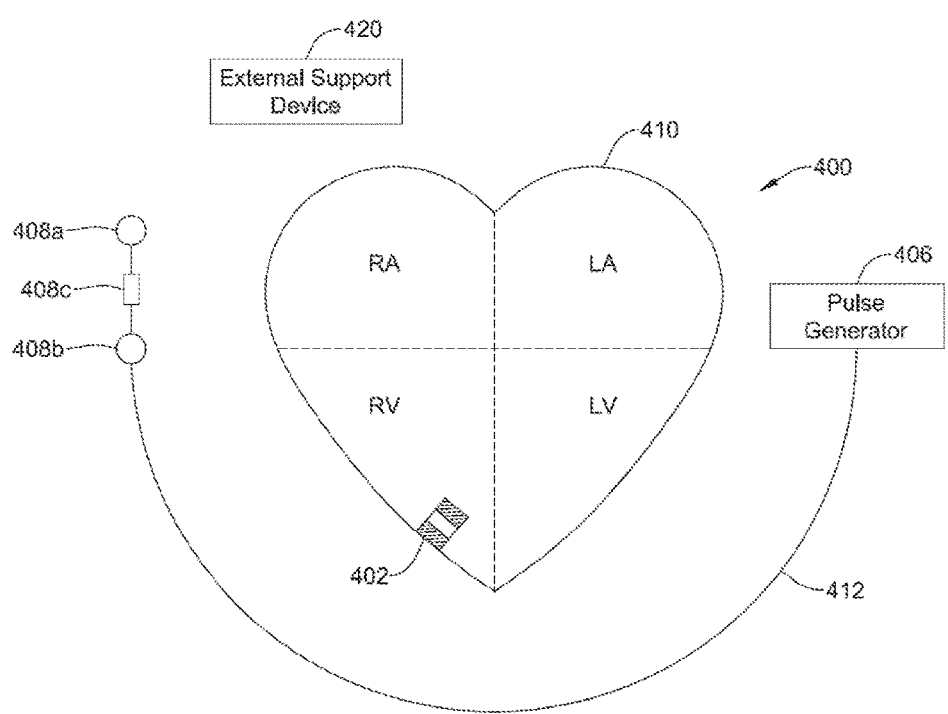
FIG. 4 is a schematic diagram of a system including an LCP and another medical device, in accordance with another embodiment of the present disclosure.

FIG. 4 depicts an illustrative medical device system 400 that may be configured to operate together. For example, system 400 may include multiple devices that are implanted within a patient and are configured to sense physiological signals, determine occurrences of cardiac arrhythmias, and deliver electrical stimulation to treat detected cardiac arrhythmias. In some embodiments, the devices of system 400 may be configured to determine occurrences of dislodgment of one or more devices of system 400. In FIG. 4, an LCP 402 is shown fixed to the interior of the right ventricle of the heart 410, and a pulse generator 406 is shown coupled to a lead 412 having one or more electrodes 408a-408c. In some cases, pulse generator 406 may be part of a subcutaneous implantable cardioverter-defibrillator (SICD), and the one or more electrodes 408a-408c may be positioned subcutaneously adjacent the heart. LCP 402 may communicate with the SICD, such as via communication pathway 308. The locations of LCP 402, pulse generator 406, lead 412, and electrodes 408a-c depicted in FIG. 4 are just exemplary. In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

Medical device system 400 may also include external support device 420. External support device 420 can be used to perform functions such as device identification, device programming and/or transfer of real-time and/or stored data between devices using one or more of the communication techniques described herein, or other functions involving communication with one or more devices of system 400. As one example, communication between external support device 420 and pulse generator 406 can be performed via a wireless mode, and communication between pulse generator 406 and LCP 402 can be performed via a conducted communication mode. In some embodiments, communication between LCP 402 and external support device 420 is accomplished by sending communication information through pulse generator 406. However, in other embodiments, communication between the LCP 402 and external support device 420 may be via a communication module.

FIG. 4 only illustrates one example embodiment of a medical device system that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different from those depicted in FIG. 4. Accordingly, it should be recognized that numerous other medical device systems, different from system 400 depicted in FIG. 4, may be operated in accordance with techniques disclosed herein. As such, the embodiment shown in FIG. 4 should not be viewed as limiting in any way.

In some embodiments, LCP 100 may be configured to operate in one or more modes. Within each mode, LCP 100 may operate in a somewhat different manner. For instance, in a first mode, LCP 100 may be configured to sense certain signals and/or determine certain parameters. In a second mode, LCP 100 may be configured to sense at least some different signals and/or determine at least some different parameters than in the first mode. In at least one mode, LCP 100 may be configured to determine a dislodgment status or determine whether dislodgment has occurred. For ease of description, a mode that includes LCP 100 being configured to determine a dislodgment status may be called a dislodgment mode. Other modes may include one or more programming and/or therapy modes, and it may be possible for LCP 100 to be engaged in multiple modes concurrently.

Figure 5:
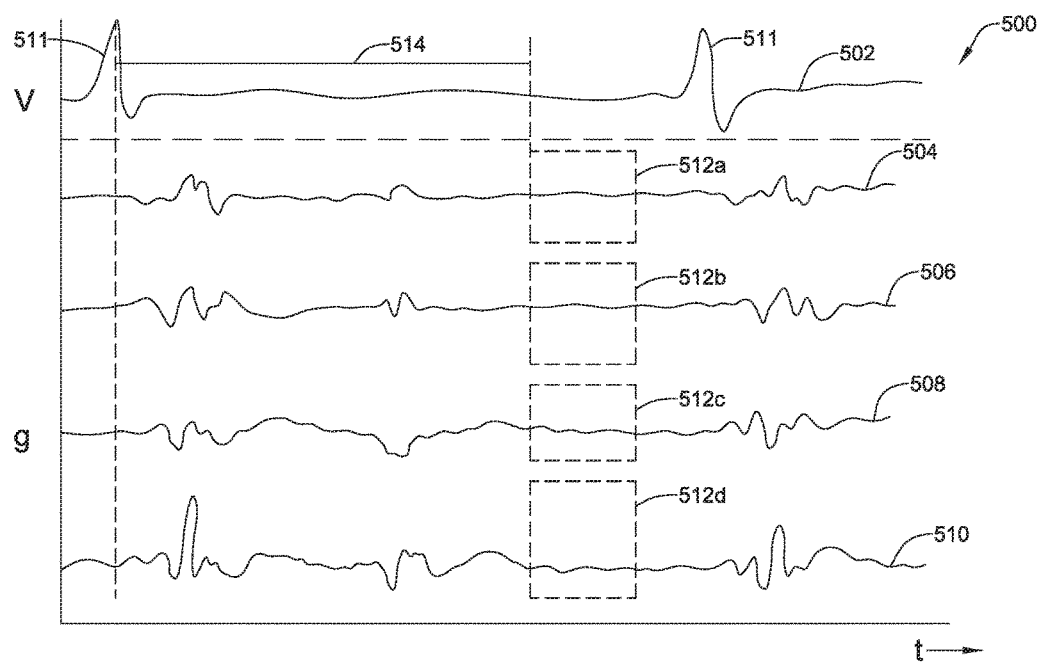
FIG. 5 is a graph showing an illustrative cardiac electrical signal and illustrative accelerometer signals, as well as sensing windows, according to one aspect of the present disclosure.

FIG. 5 is a graph 500 showing illustrative signal tracings that represent signals sensed or generated by LCP 100 during a time period when LCP 100 is attached to a wall of a patient's heart and not operating in a dislodgment mode. In the example shown in FIG. 5, signal 502 represents a cardiac electrical signal sensed by LCP 100. Signals 504, 506, and 508 all represent signals from different axes generated by a three-axis accelerometer of LCP 100. Signal 510 represents an accelerometer magnitude signal, which may be determined by summing signals 504, 506, and 508 or summing the absolute values of signals 504, 506, and 508. In other embodiments, signal 510 may represent a different signal generated by another combinations of signals 504, 506, and 508, such as a root-mean-square or root-sum-square of signals 504, 506, and 508, or any other derivation of signals 504, 506, and 508 as desired. While various accelerometer signals 504, 506, 508 and 510 are shown, it is contemplated that less or more accelerometer signals may be used.

LCP 100 may be configured to sense one or more of signals 504, 506, 508 and/or 510, or generate one or more of signals 504, 506, 508 and/or 510 via the accelerometer, during predetermined time periods. For instance, to sense signals 504, 506, 508 and/or 510, LCP 100 may be configured to receive signals 504, 506, 508 and/or 510 at processing module 110. In some embodiments, LCP 100 may connect an output of the accelerometer to processing module 110 during the time periods where LCP 100 is sensing signals 504, 506, 508 and/or 510. In other embodiments, the accelerometer may be configured to actively output signals 504, 506, 508 and/or 510 during the time periods where LCP 100 is sensing signals 504, 506, 508 and/or 510, for example using a communication link connecting processing module 110. Where processing module 110 is a digital device, sensing signals 504, 506, 508 and/or 510 may include sampling signals 504, 506, 508 and/or 510, which may be done by processing module 110, or the accelerometer may communicate signal samples to processing module 110. In other embodiments, LCP 100 may control the generation of signals 504, 506, 508 and/or 510 by the accelerometer. For instance, LCP 100 may control when power is delivered to the accelerometer, and the accelerometer may only generate signals 504, 506, 508 and/or 510 when power is delivered to the accelerometer, or the accelerometer may only provide a substantial signal at an output during times where power is delivered to the accelerometer. In some cases, LCP 100 may switch the accelerometer from a lower-power state to a higher-power state during time periods where LCP 100 senses the accelerometer signal. During the lower-power state, the accelerometer may not provide an appreciable signal at an output for LCP 100 to sense.

LCP 100 may be configured to sense one or more signals during predetermined time periods. Such predetermined time periods may be represented by, for example, sensing periods 512a-512d in FIG. 5. Sensing periods 512a-512d may occur at regular intervals, such as every five seconds, every second, every eight hundred milliseconds, every seven hundred milliseconds, or any other suitable interval. Alternatively, LCP 100 may initiate sensing periods 512a-512d after every beat, once every other beat, once every five beats, or at any other suitable frequency. In at least some cases, LCP 100 may adjust the timing of the intervals according to a heart rate of the patient such that sensing periods 512a-512d occur during the same portion of each successive cardiac cycle.

In some cases, LCP 100 may implement sensing periods 512a-512d based on one or more detected features of cardiac electrical signal 502. For instance, LCP 100 may detect one or more features of cardiac electrical signal 502, such as cardiac electrical events 511. Cardiac electrical events 511 may, in some cases, represent R-waves or other morphological features that may be detected by LCP 100. Upon detection of a cardiac electrical event 511, LCP 100 may initiate a time delay, such as time delay 514. Upon expiration of time delay 514, LCP 100 may initiate sensing periods 512a-512d, during which LCP 100 may sense one or more of signals 504, 506, 508 and 510. In some cases, LCP 100 may adjust time delay 514 based on the heart rate of the patient. For instance, when the heart rate is at a relatively higher rate, LCP 100 may shorten time delay 514, and when the heart rate is at a relatively lower rate, LCP 100 may lengthen time delay 514. This may help to ensure that LCP 100 consistently initiates sensing periods 512a-512d during the same or similar portion of each cardiac cycle.

In some embodiments, the length of time delay 514 may be chosen to align with a portion of the cardiac cycle where the heart is relatively mechanically inactive, such as shown in FIG. 5. For instance, time delay 514 may be chosen so that it expires between about fifty milliseconds to about one-hundred fifty milliseconds before the beginning of a next cardiac electrical event 511. In other embodiments, time delay 514 may be chosen so that it expires between about three hundred milliseconds and about eight hundred milliseconds after a detected cardiac electrical event 511. In more specific examples, time delay 514 may have a value of about three-hundred fifty milliseconds, about four-hundred milliseconds, about five-hundred milliseconds, about six-hundred milliseconds, about seven-hundred milliseconds, about eight-hundred milliseconds, or any other suitable value. These timings may ensure that sensing periods 512a-512d occur after repolarization of the heart during a cardiac cycle, but before a polarization event during the subsequent cardiac cycle.

By sensing signals 504, 506, 508 and/or 510 during sensing periods 512a-512d, LCP 100 may collect a first amount of accelerometer signal data during a cardiac cycle. For instance, the first amount of accelerometer data may represent a certain length of signals 504, 506, 508 and/or 510 sensed during sensing periods 512a-512d or a certain number of accelerometer signal samples.

The accelerometer data collected during sensing periods 512a-512d may aid LCP 100 in determining one or more patient parameters. For instance, during the portion of the cardiac cycle represented by sensing periods 512a-512d in FIG. 5, the heart muscle may be in a relatively relaxed state while filling with blood. Accordingly, during this portion of the cardiac cycle, the orientation of LCP 100, and hence the accelerometer within LCP 100, may be disposed at a relatively consistent position. This may facilitate LCP 100 in determining a posture of the patient and/or an activity level of the patient by minimizing any movement caused by the contraction of the heart.

To determine a posture of the patient, LCP 100 may compare the accelerometer signal captured during such a sensing period with a stored template accelerometer signal. For example, LCP 100 may be initially programmed by orienting a patient in a first posture and sensing the accelerometer signal (relative to gravity) during one or more sensing periods while the patient is in the first posture. LCP 100 may store the sensed accelerometer signal in memory. In some cases, this may be repeated several times. In either cases, the LCP may generate an accelerometer signal template for that posture. This process may be repeated for different postures. LCP 100 may then compare current sensed accelerometer signals to the stored accelerometer signal templates to determine the current posture of the patient.

In some additional or alternative embodiments, LCP 100 may track a patient activity parameter using the accelerometer signal sensed during the sensing periods 512a-512d. To determine a patient activity parameter, LCP 100 may determine a difference between the sensed or sampled current accelerometer signal and a previously sensed or sampled accelerometer signal. LCP 100 may generate an activity parameter based at least in part on this determined difference. In some cases, LCP 100 may store the determined difference and may generate new determined differences on a rolling basis as LCP 100 sensed or samples new current accelerometer signals. When so provided, LCP 100 may determine a patient activity parameter from multiple of these determined differences. For instance, LCP 100 may sum the differences together over a rolling period of time to produce a patient activity parameter. LCP 100 may then compare the patient activity parameter to one or more thresholds to determine an activity level of the patient.

In some instances, LCP 100 may use either or both of the determined posture and patient activity parameter to adjust delivery of therapy to the heart. For instance, where LCP 100 is a pacemaker and configured to deliver electrical stimulation pulses to the heart of the patient, LCP 100 may adjust the rate of delivery of electrical stimulation pulses based on the posture and/or activity parameter. For example, LCP 100 may decrease the rate of delivery of electrical stimulation pulses after determining that a patient has transitioned from a standing posture to a sitting posture. In other example, LCP 100 may be configured to increase the rate of delivery of electrical stimulation pulses after determining an increase in the value of the patient activity parameter. It should be understood that these are only a few examples of how LCP 100 may adjust the delivery of therapy based on the determined posture and/or patient activity parameter.

Figure 6:
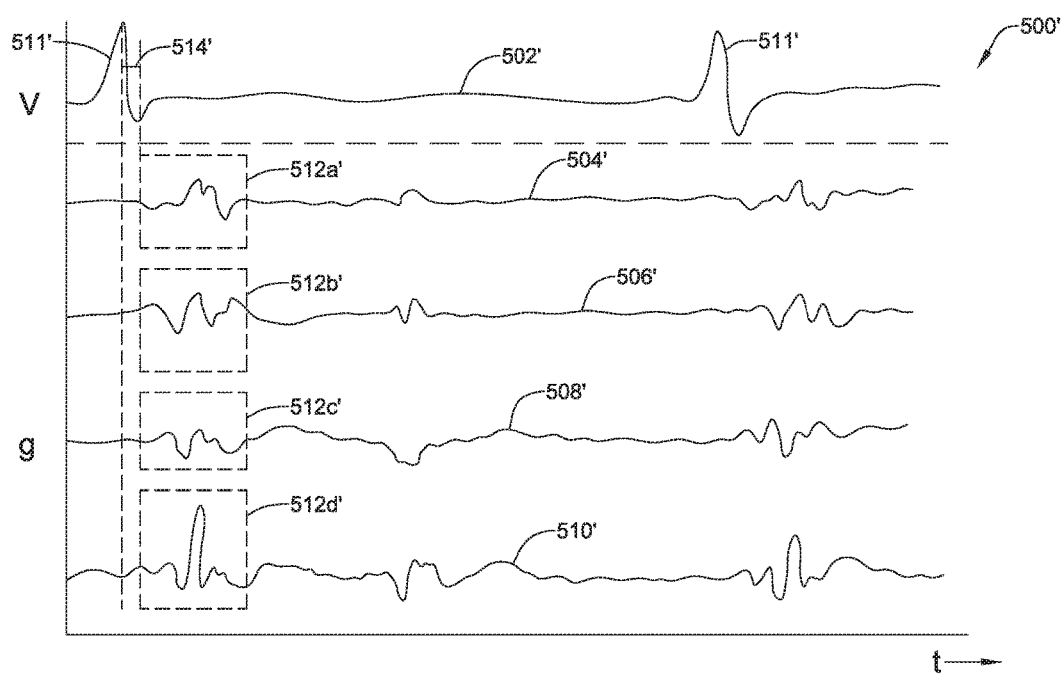
FIG. 6 is a graph showing an illustrative cardiac electrical signal and illustrative accelerometer signals, as well as sensing windows, according to another aspect of the present disclosure.

As mentioned, when LCP 100 is in a dislodgment mode, LCP 100 may sense the accelerometer signal(s) differently. FIG. 6 depicts graph 500' illustrating an example cardiac electrical signal 502', accelerometer signals 504', 506', 508' and 510', and sensing periods 512a'-512d' during which LCP 100 may sense the accelerometer signals in a dislodgement mode.

As can be seen, time delay 514' of FIG. 6 is relatively shorter than time delay 514 of FIG. 5. The length of time delay 514' may be chosen to generally align with the contraction of the heart. For instance, time delay 514' may be chosen so that sensing periods 512a'-512d' fall during a polarization event of the heart. In other embodiments, time delay 514' may be chosen so that sensing periods 512a'-512d' fall just after a polarization event of the heart, but still capture the mechanical motion of the heart during contraction. Although not shown in FIG. 6, in some cases when in a dislodgment mode, LCP 100 may also sense accelerometer signals 504', 506', 508' and 510' during sensing periods corresponding to sensing periods 512a-512d in order to still obtain information related to patient posture and/or activity, if desired.

In some instances, time delay 514' may be about zero milliseconds, about five milliseconds, about ten milliseconds, about fifteen milliseconds, about twenty milliseconds, about twenty-five milliseconds, about thirty milliseconds, about forty milliseconds, or about fifty milliseconds, or any other suitable period of time. In general, time delay 514' may have a value that is less than an electromechanical delay of the heart, which is the delay between when LCP 100 detects a cardiac electrical event 511' (e.g. R-wave) and an onset of cardiac wall motion or a threshold amount of cardiac wall motion. In some additional or alternative embodiments, time delay 514' may have a length that changes along with the heart rate of the patient. As one example, for relatively higher heart rates, time delay 514' may be shorter than for relatively lower heart rates.

When in a dislodgment mode, LCP 100 may collect a second amount of accelerometer signal data during a cardiac cycle that is greater than the first amount of accelerometer signal data that LCP 100 collects when not in a dislodgment mode. For instance, sensing periods 512a'-512d' may be longer than sensing periods 512a-512d such that the lengths of signals 504, 506, 508 and/or 510 in sensing periods 512a'-512d' is longer than the lengths of signals 504, 506, 508 and/or 510 within sensing periods 512a-512d. In some cases, where LCP 100 collects signal samples, the number of samples collected during sensing periods 512a'-512d' may be greater than the number of signals collected during sensing periods 512a-512d. Alternatively, the second amount of accelerometer signal data may be greater than the first amount of accelerometer signal data due to LCP 100 collecting accelerometer signal data during both sensing periods 512a'-512d' and sensing periods 512a-512d.

In general, LCP 100 may be able to use accelerometer signals sensed during a portion of the cardiac cycle that corresponds to sensing periods 512a'-512d' to help determine a dislodgment status. For example, LCP 100 may be configured to sense one or more signals, determine one or more parameters, and based on the determined one or more parameters, determine whether dislodgment (e.g. partial and/or full) has occurred. The following techniques described various illustrative ways in which LCP 100 may determine a dislodgment status based on one or more of such sensed signals.

Throughout this description, LCP 100 is described as the device sensing signals, determining parameters, and determining whether dislodgment has occurred. However, where LCP 100 is part of a system, such as system 400, the sensing of signals, determining parameters, and/or determining whether dislodgment has occurred may be split up in any manner between any combinations of devices of system 400. For instance, LCP 100 may sense one or more signals and communicate those signals to another device, such as external support device 420. External support device 420, then, may determine one or more parameters based on the signals received from LCP 100. In some further embodiments, external support device 420 may be further configured to determine whether dislodgment has occurred based on those parameters. However, this is only one example contemplated by this disclosure how the sensing and determining processes may be split up amongst the devices of a system. In still other examples, the disclosed techniques may be performed by devices other than a leadless cardiac pacemaker. For instance, devices such as MD 200 which have accelerometers included in a tip of a lead may perform the disclosed techniques. In these embodiments, MD 200 may have a lead with an accelerometer in the lead tip implanted within a chamber of the heart and attached to a heart wall. In this manner, these devices may be able to use sensed accelerometer signals in accordance with the disclosed techniques to determine a dislodgment status of the implanted lead.

When part of a system, LCP 100 may enter a dislodgment mode based on a signal communicated from another device, for example external support device 420. In other embodiments, LCP 100 may be configured to enter a dislodgment mode periodically. For instance, LCP 100 may be configured to enter a dislodgment mode once an hour, once a day, once a week, once a month, or any other suitable time period.

In order to determine a dislodgment status, LCP 100 may be configured to sense a dislodgment metric. In some examples, the dislodgment metric may be an accelerometer signal. For instance, as described, LCP 100 may include an accelerometer. FIGS. 7-10 describe various techniques of how LCP 100 may use signals sensed from the accelerometer to determine a dislodgment status.

Figure 7:
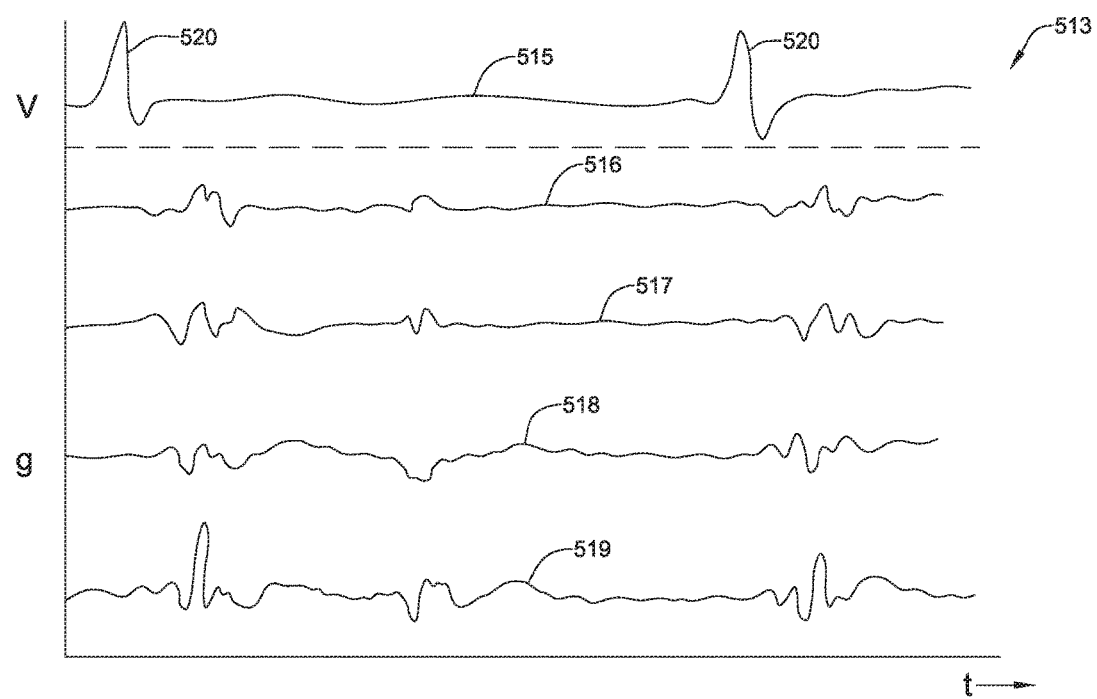
FIG. 7 is a graph showing an illustrative cardiac electrical signal and illustrative accelerometer signals sensed by an implantable device with an accelerometer securely attached to a heart wall.

FIG. 7 is a graph 513 showing illustrative signals taken during a time period when an LCP 100 was securely attached to a wall of a heart. Signal 515 represents an illustrative cardiac electrical signal sensed by LCP 100. Signals 516, 517, and 518 represent illustrative accelerometer signals from different axes generated by the three-axis accelerometer of LCP 100 of the LCP 100. Signal 519 represents an accelerometer magnitude signal, which may be determined by summing accelerometer signals 516, 517, and 519 or summing the absolute values of accelerometer signals 516, 517, and 519. In other embodiments, signal 519 may represent a different signal generated by other combinations of signals 516, 517, and 518, such as a root-mean-square or root-sum-square of signals 516, 517, and 518, or any other derivation of signals 516, 517, and 518. While various accelerometer signals 516, 517, 518 and 519 are shown, it is contemplated that less or more accelerometer signals may be used.

As can be seen from FIG. 7, when LCP 100 is securely attached to a heart wall, there is a synchronicity between cardiac electrical events 520 and the motion of LCP 100, as indicated by signals 516, 517, 518, and 519, with larger deflections in 516, 517, 518, and 519 occurring shortly after cardiac electrical events 520. As the cardiac electrical signals propagate through the heart, the cardiac electrical signals cause a contraction of the heart, thereby causing motion of LCP 100, as represented by accelerometer signals 516, 517, 518, and 519.

Figure 8:
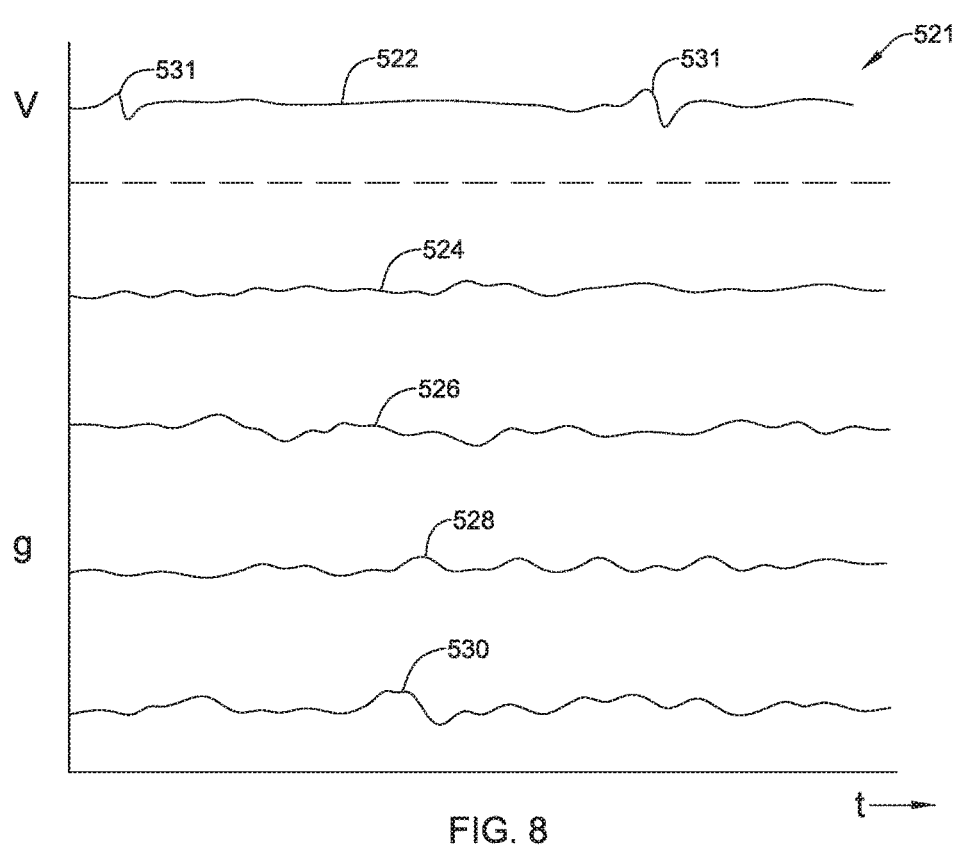
FIG. 8 is a graph showing an illustrative cardiac electrical signal and illustrative accelerometer signals sensed by an implantable device with an accelerometer at least partially dislodged from a heart wall.

FIG. 8 is a graph 521 that shows an illustrative cardiac electrical signal 522 and illustrative accelerometer signals 524, 526, 528, and 530, similar to that shown in FIG. 7. Signals 522, 524, 526, 528, and 530 represent signals taken during a time period where LCP 100 has become at least partially dislodged from the wall of the heart. As can be seen, there is much less synchronicity between the occurrences of cardiac electrical events 531 and the motion of LCP 100, as represented by accelerometer signals 522, 524, 526, 528, and 530. Since LCP 100 has become at least partially dislodged from the heart wall, the motion of LCP 100 is at least partially disassociated with the motion of the heart wall.

Accordingly, LCP 100 can be configured to determine one or more parameters based on the signals of the accelerometer of LCP 100, and use these one or more parameters to determine a dislodgment status of the LCP 100. In one example, LCP 100 may determine a dislodgment metric and, based at least in part on the dislodgment metric, determine a dislodgment status, e.g. whether dislodgment (e.g. partial or full) has occurred or whether dislodgment has not occurred. In the examples of FIGS. 7-10, the dislodgment metric may be related to a sensed accelerometer signal, but as described with respect to other figures, the dislodgment metric may be related to other sensed signals or parameters, depending on the circumstances.

In at least some embodiments where the dislodgment metric is based at least in part on an accelerometer signal, LCP 100 may sense and store a template accelerometer signal when LCP 100 is securely attached to the heart wall. To generate the template, the LCP 100 may sense the accelerometer signal during a sensing period, such as sensing periods 512a'-512d', and store the sensed accelerometer signal(s) in memory for use as a template.

Figure 9:
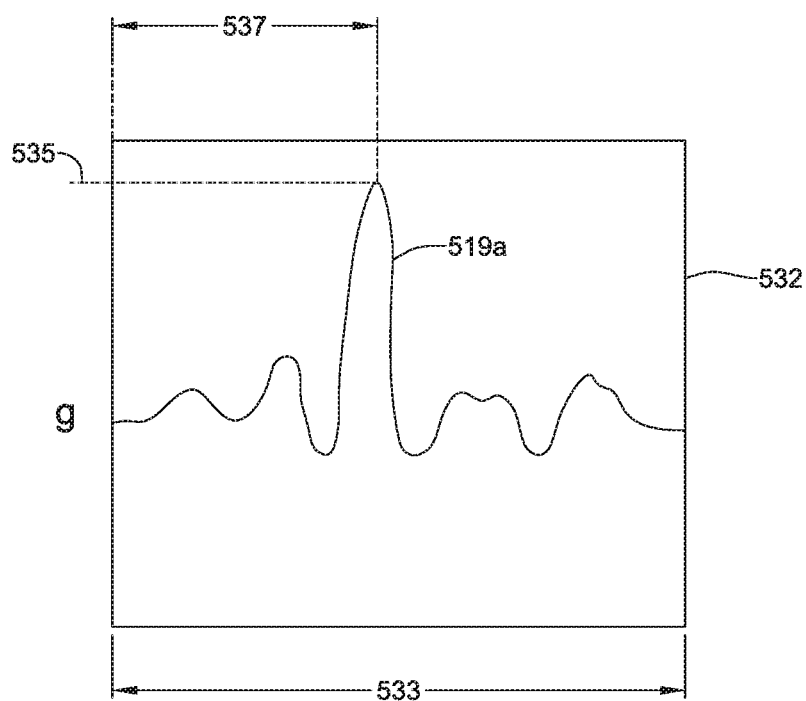
FIG. 9 shows a sensing window that includes a portion of an accelerometer signal of FIG. 7.

FIG. 9 depicts an example sensing window 532 and illustrative accelerometer signal 519a, which may represent a portion of accelerometer signal 519 from FIG. 7 that fell within a sensing period such as sensing period 512d' of FIG. 6. Recall that FIG. 7 is a graph 513 showing illustrative signals taken during a time period when an LCP 100 was securely attached to a wall of a heart. It is contemplated that the length 533 of sensing window 532, which may correspond to the lengths of sensing periods 512a'-512d', may vary from between about 50 ms to about 200 ms, and in some specific embodiments, length 533 may be 50 ms, 100 ms, 150 ms, or 200 ms, or any other suitable value. In some cases, sensing window 532 may be substantially longer, for instance, about half of a cardiac cycle of the patient, about three quarters of the cardiac cycle of the patient, or may span an entire cardiac cycle. In some additional or alternative embodiments, length 533 may have a value that changes with the heart rate of the patient. As one example, for relatively higher heart rates, length 533 may be shorter than for relatively lower heart rates.

LCP 100 may determine one or more features of signal 519a. For instance, LCP 100 may determine a maximum value of signal 519a, represented by maximum value 535 (maximum gravity, or "g" value). In some instances, LCP 100 may determine a time difference between the beginning of sensing window 532 and maximum value 535 of signal 519a, represented by time difference 537. In some cases, LCP 100 may determine an integral of signal 519a. These are just some example. In general, signal 519a may represent an accelerometer signal template captured when the LCP 100 is securely attached to the heart wall, and each parameter determined by LCP 100 based on the accelerometer signal template may represent a baseline parameter.

Figure 10:
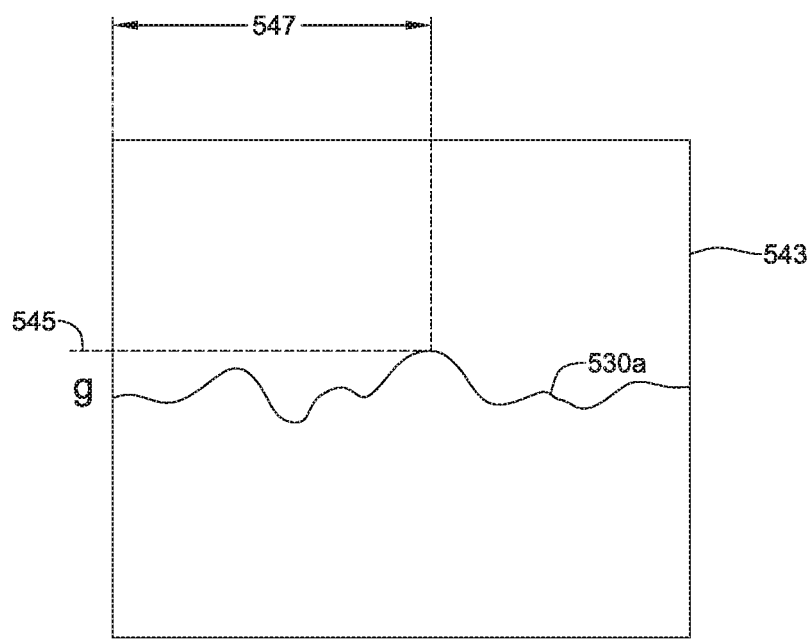
FIG. 10 shows a sensing window that includes a portion of an accelerometer signal of FIG. 8.

FIG. 10 depicts sensing window 543 including an illustrative signal 530a, which may represent a portion of signal 530 from FIG. 8 that was within a sensing period such as sensing period 512d' of FIG. 6. Recall that FIG. 8 is a graph 521 showing illustrative signals taken during a time period when an LCP 100 was at least partially dislodged from the wall of the heart. Like signal 519a, LCP 100 may determine one or more features of signal 530a, such as a maximum amplitude, represented by maximum amplitude 545, a time difference parameter, represented by time difference 547, or an integral of signal 530a.

LCP 100 may determine a correlation parameter(s) between signals 519a and 530a, and/or between one or more of the determined features of signals 519a and 530a. For example, in some embodiments, LCP 100 may perform one or more correlation analyses, such as a cross-correlation analysis, on signals 519a and 530a to produce a correlation parameter representing a relative similarity between signals 519a and 530a. LCP 100 may additionally, or alternatively, determine a difference between one or more of the determined features of signals 519a and 530a, resulting in one or more correlation parameters. In some instances, the correlation parameter may be a percentage determined by LCP based on features of signals 519a and 530a. LCP 100 may compare the determined correlation parameter(s) to a threshold value(s). If the correlation parameter is above or below a threshold value, depending on which correlation parameter is used, LCP 100 may determine that dislodgment (partial or full) has occurred.

Where LCP 100 uses a correlation analysis to produce a correlation parameter, the correlation parameter may vary between zero and one, with zero representing no correlation between signals 519a and 530a, and one representing perfect correlation between 519a and 530a, LCP 100 may determine a dislodgment status of dislodged if the determined correlation parameter is below a threshold, for example about 0.7. This is just one example, and it is contemplated that other threshold values may be used, such as about 0.5, about 0.6, about 0.8, or any other suitable value.

As mentioned, in additional or other embodiments, LCP 100 may determine a difference between time difference 537 and 547. LCP 100 may determine that dislodgment has occurred if the absolute value of this difference is greater than a threshold, such as 15 ms. This is just one example, and it is contemplated that other threshold values may be used, such about 5 ms, about 10 ms, about 20 ms, about 25 ms, about 30 ms, or about 40 ms, or any other suitable value. Where LCP 100 initiates sensing windows 532 and 543 at the same time in relation to a detected cardiac event, a larger difference between 537 and 547 may indicate a greater lack of synchrony between cardiac electrical events and the mechanical motion of the heart, which may be one indication that dislodgment has occurred.

Where LCP 100 determines a difference between maximum amplitudes 535 and 545, LCP 100 may determine that dislodgment has occurred if the absolute value of the difference is greater than a threshold, such as a threshold of about 0.4 g (3.92 m/s$^2$). This is just one example, and it is contemplated that other threshold values may be used, such about 0.1 g (0.98 m/s$^2$), about 0.2 g (1.96 m/s$^2$), about 0.3 g (2.94 m/s), about 0.5 g (4.90 m/s$^2$), or any other suitable value.

Although these described embodiments include specific values for the threshold values, in other embodiments, LCP 100 may use percentages. For instance, LCP 100 may determine by what percentage a feature of signal 530a differs from the same feature of signal 519a. LCP 100 may then compare the determined percentage to a threshold percentage to determine whether dislodgment has occurred. In some embodiments, LCP 100 may determine that dislodgment has occurred if the feature of signal 530a differs from the same feature of signal 519a by a threshold of about twenty-five percent or more. In other embodiments, different threshold percentages may be used, such as about ten percent, about fifteen percent, about twenty percent, about thirty percent, about forty percent or any other suitable percentage value.

In some alternatives to using a single instance of a difference between maximum amplitudes, LCP 100 may determine a trend of the different between maximum amplitudes. For example, LCP 100 may track a moving average difference between maximum amplitudes over multiple cardiac cycles, such as five, eight, ten, fifteen cardiac cycles, or twenty cardiac cycles, or any other suitable number of cardiac cycles. LCP 100 may determine a baseline average difference between maximum amplitudes of the accelerometer signal during a baseline time period or based on a sensed accelerometer template. Then, LCP 100 may compare the determined moving average to the baseline average difference. If the moving average falls below a certain percentage of the baseline average difference, such as below about five percent, about ten percent, about fifteen percent, about twenty percent, about twenty-five percent, about thirty percent, about forty percent, or about fifty percent, or any other suitable percent, LCP 100 may determine that dislodgment has occurred.

Where LCP 100 determines a difference between the integrals of signals 519a and 530a, LCP 100 may determine that dislodgment has occurred if the absolute value of the difference is greater than a threshold of about twenty-five percent of the integral of signal 519a. However, other threshold values may be used in other embodiments, such as about ten percent, about fifteen percent, about twenty percent, about thirty percent, about forty percent about fifty percent, or any other suitable value.

In some embodiments, LCP 100 may determine multiple correlation parameters, for instance using any of the maximum amplitude of the accelerometer signal, the time interval between the beginning of a sensing period and a peak of the accelerometer signal, and the integral of the accelerometer signal. In such embodiments, LCP 100 may determine a dislodgment status of dislodged if any of the correlation parameters indicate dislodgment, for example by being above or below a corresponding threshold value. In other embodiments, LCP 100 may determine a dislodgment status of dislodged only if analysis of two (or more) features indicate dislodgment has occurred. In still other embodiments, LCP 100 may determine dislodgment only if all determined correlation parameters indicate dislodgment has occurred.

Although the above techniques were described with respect to a signal representing the magnitude of the accelerometer signal, in other embodiments, LCP 100 may perform a similar analysis on each sensed accelerometer signal, such as any of using signals 504, 506, and/or 508. In this manner, LCP 100 may determine whether dislodgment has occurred based on any channel of the accelerometer, or based on the magnitude of the accelerometer signal. In at least some embodiments, LCP 100 may only determine a dislodgment status of dislodged if analysis on multiple signals of the accelerometer indicates that dislodgment has occurred.

Further, a similar analysis may be used in at least some embodiments where LCP 100 includes a gyroscope. For instance, gyroscopes measure changes in the rate of angular velocity and may output signals representative of the changes in the rate of angular velocity. When LCP 100 is attached to a heart wall, signals generated by a gyroscope may have a synchronicity with cardiac electrical signals, in a similar manner to that described above for accelerometer signals. When LCP 100 is dislodged, the gyroscope signals may lose their synchronicity with the cardiac electrical signals, and this difference may be used by LCP 100 to determine a dislodgment status. Accordingly, in some embodiments, LCP 100 may employ any of the analyses above described with respect to accelerometer signals to gyroscope signals to determine a dislodgment status.

Figure 11A:
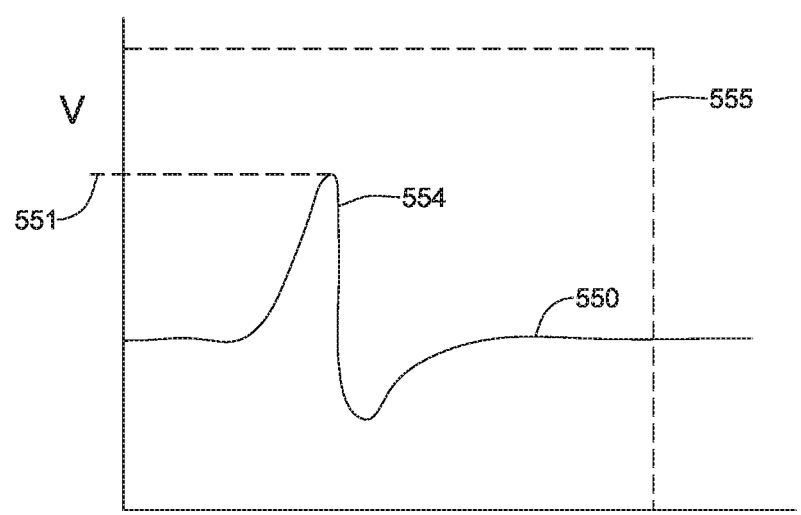
FIG. 11A shows an illustrative cardiac electrical signal sensed by an implantable device that is securely attached to a cardiac wall.
Figure 11B:
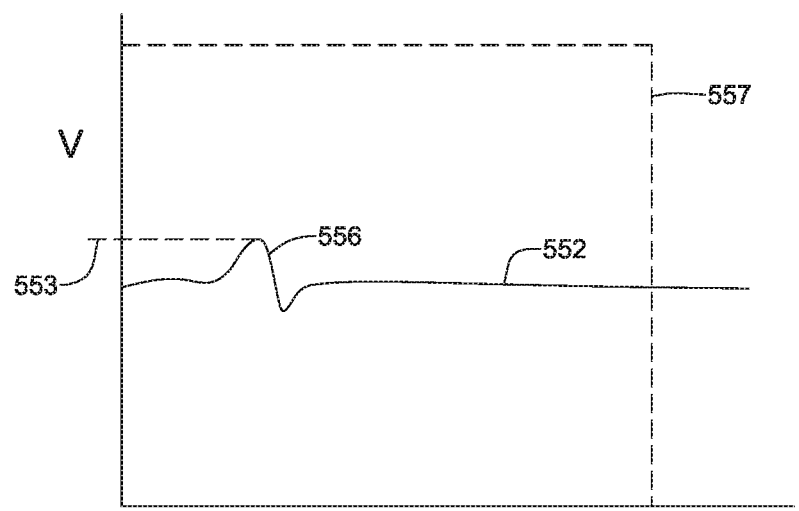
FIG. 11B shows an illustrative cardiac electrical signal sensed by an implantable device that is at least partially dislodged from a cardiac wall.

In some instances, the dislodgment metric may include the sensed cardiac electrical signals. FIGS. 11A and 11B depict example cardiac electrical signals, signals 550 and 552, including cardiac electrical events 554 and 556. Cardiac electrical signal 550 may be sensed by LCP 100 when LCP 100 is securely attached to a heart wall and cardiac electrical signal 552 may be sensed when LCP 100 is at least partially dislodged from the cardiac wall. As can be seen, dislodgment of LCP 100 may impact an amplitude of sensed cardiac electrical events, as indicated by event amplitudes 551 and 553.

In a similar manner to the accelerometer signal of FIGS. 9 and 10, LCP 100 may determine a correlation parameter based on one or more features of cardiac electrical signals 550 and 552. For instance, LCP 100 may perform one or more correlation analyses, such as a cross-correlation analysis on signals 550 and 552, and more specifically on portions of signals 550 and 552 falling within sensing windows 555 and 557, resulting in a correlation parameter. In these embodiments, LCP 100 may determine that dislodgment has occurred if the correlation parameter is less than a threshold of about 0.75, or less than a threshold of about 0.6, about 0.7, about 0.8, about 0.85, or any other suitable value in other embodiments.

Additionally, or alternatively, LCP 100 may determine a maximum amplitude of signals 550 and 552, represented by maximum amplitudes 551 and 553, respectively. LCP 100 may then determine a difference of these values, resulting in a correlation parameter. In these embodiments, LCP 100 may determine that dislodgment has occurred if the absolute value of the difference between maximum values 551 and 553 is greater than a threshold value of about 20 mV. This is just one example, and it is contemplated that other threshold values may be used, such as about 10 mV, about 15 my, about 25 mV, about 30 mV, or any other suitable value. Of course, as mentioned before, instead of relying on a single instance to determine that dislodgment has occurred, LCP 100 may track a moving average of maximum amplitudes of the cardiac electrical signal. LCP 100 may then compare this moving average to an averaged maximum value template value to determine whether dislodgment has occurred.

In some embodiments, the correlation parameter may be a percentage. For instance, LCP 100 may determine a percentage based on maximum amplitudes 551 and 553, such as by what percentage maximum amplitude 553 varies from maximum amplitude 551, or what percentage of maximum amplitude 551 maximum amplitude 553 represents. LCP 100 may then compare the determined correlation parameter to a threshold percentage to determine a dislodgment status. In these embodiments, LCP 100 may determine that dislodgment has occurred if the correlation parameter is greater than a threshold value of about ten percent, about fifteen percent, about twenty percent, about twenty-five percent, about thirty percent, or about forty percent, or any other suitable value. In general, LCP 100 may determine a correlation parameter and determine whether dislodgment has occurred using cardiac electrical signals in a manner similar to any process described with respect to the accelerometer signal of FIGS. 9 and 10.

In other embodiments, the dislodgment metric may be or include temperature. For instance, LCP 100 may include a temperature sensor as part of mechanical sensing module 108. In some embodiments, LCP 100 may include at least two temperature sensors separated by a distance. A first temperature sensor may be located in a proximal portion LCP 100, and a second temperature sensor may be located in a distal portion of LCP 100. When LCP 100 is implanted, LCP 100 may be oriented such that the second temperature sensor may be disposed proximate the heart wall while the first temperature sensor is disposed away from the heart wall. In these embodiments, the two temperature sensors may experience a temperature differential due to the second temperature sensor being located more closely to metabolically active heart tissue. Where LCP 100 is dislodged, the temperature differential may lessen or may go away as the second temperature sensor is no longer secure proximate the heart tissue.

Figure 12:
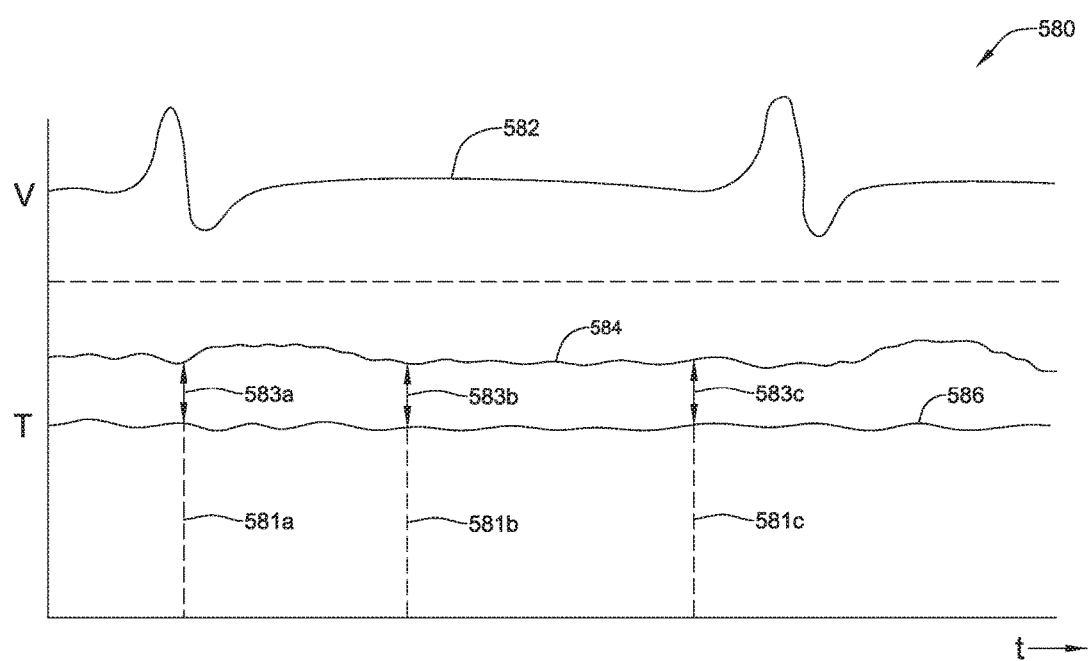
FIG. 12 is a graph showing an illustrative cardiac electrical signal, a first temperature sensor signal and a second temperature sensor signal plotted on a common time axis.

Accordingly, readings taken from each temperature sensor at the same time may allow for determination of a dislodgment status. FIG. 12 depicts a graph 580 showing an illustrative cardiac electrical signal 582, a first temperature sensor signal 586, and a second temperature sensor signal 584. In the example of FIG. 12, LCP 100 may take measurements of first temperature sensor signal 586 and second temperature sensor signal 584 periodically, such as at times 581a, 581b, and 581c. Although FIG. 12 shows LCP 100 taking three temperature measurements within a cardiac cycle, in other embodiments the measurement frequency may be any suitable value. Once LCP 100 has measured first temperature sensor signal 586 and second temperature sensor signal 584, LCP 100 may determine a correlation parameter, represented by temperature differentials 583a, 583b, and 583c. For instance, LCP 100 may determine a difference between first temperature sensor signal 586 and second temperature sensor signal 584, resulting in a correlation parameter. LCP 100 may then compare the temperature differential to a temperature differential threshold value. If the temperature differential is less than the temperature differential threshold value, LCP 100 may determine that dislodgment has occurred. In some embodiments, the temperature differential threshold may be about 0.2 degrees C. However, in other embodiments, the temperature differential threshold may be about 0.1 degrees C., about 0.15 degrees C., about 0.25 degrees C., about 0.3 degrees C., or any other suitable value. In at least some of these embodiments, LCP 100 may only determine that dislodgment has occurred if multiple temperature differentials are less than the temperature differential threshold, such as two, three, four, or five temperature differentials. In other embodiments, LCP 100 may determine that dislodgment has occurred if two out of three, three out of four, three out of five, or four out of five consecutive temperature differentials are lower than the temperature differential threshold.

In alternative embodiments, LCP 100 may determine a correlation parameter based on first temperature sensor signal 586 and/or second temperature sensor signal 584 in any manner similar to those described with respect to the accelerometer signal of FIGS. 9-10. For example, LCP 100 may perform one or more correlation analysis on first temperature sensor signal 586 and/or second temperature sensor signal 584 in relation to a stored first temperature sensor signal template and/or a stored second temperature sensor signal template to produce a correlation parameter. In other embodiments, LCP 100 may determine a correlation parameter that is percentage related to a comparison of first temperature sensor signal 586 and second temperature sensor signal 584.

In still other embodiments, the dislodgment metric may be or include impedance. For instance, an impedance sensed by LCP 100 may differ when LCP 100 is attached to a wall of a heart and when LCP 100 is dislodged. In these embodiments, LCP 100 may deliver one or more electrical pulses into the tissue of the patient and determine an impedance based on signals sensed during or after delivering an electrical pulse. LCP 100 may determine a baseline impedance while LCP 100 is securely attached to a heart wall. LCP 100 may then periodically determine an impedance, for example once every cardiac cycle, and determine a correlation parameter based on the current sensed impedance and the baseline impedance. For instance, LCP 100 may determine a correlation parameter in any manner similar to that described with respect to accelerometer signal of FIGS. 9-10, the cardiac electrical signal of FIG. 11A-1, or the temperature signal of FIG. 12. LCP 100 may then compare the correlation parameter to one or more thresholds and determine a dislodgment status based on the comparison, again in any manner similar to that described with respect to FIGS. 9-12.

In at least some of these embodiments, the impedance may be a cardiac cycle average impedance. For instance, LCP 100 may make multiple impedance measurements over the course of a cardiac cycle, and produce an average impedance based on the measurements. LCP 100 may base the beginning of a cardiac cycle on one or more sensed features in the cardiac electrical signal, such as cardiac electrical events or other waveform features.

In more alternative embodiments, the dislodgment metric may be or include a device orientation. For instance, in at least some cases LCP 100 may be in a dislodgment mode while implanted within a patient during an implantation procedure. During the implantation procedure, the patient may remain laying in a steady position for the duration of the procedure. Accordingly, during the procedure, after implantation, LCP 100 may maintain a relatively constant orientation with respect to gravity. Subsequent deviation from this orientation may indicate dislodgment from the implanted location.

Where LCP 100 includes a three-axis accelerometer, LCP 100 may be able to determine an orientation of LCP 100 with respect to gravity. LCP 100 may then monitor the device orientation on a continuous or periodic basis, such as once per cardiac cycle or other suitable frequencies, for variations in the orientation of LCP 100 with respect to gravity. In at least some embodiments, LCP 100 may measure the orientation of LCP 100 with respect to gravity in a middle of a cardiac cycle while the heart is filling with blood. For instance, LCP 100 may begin a timer upon detection of a cardiac electrical event. When the timer expires or reaches a predetermined value, such as 500 ms, LCP 100 may determine an orientation of LCP 100 with respect to gravity. LCP 100 may use other timer values in other embodiments, and in some embodiments, the timer may be adjusted based on a heart rate of the patient. This may help to ensure that LCP 100 determines an orientation with respect to gravity while the heart is not in the middle of a contraction or other significant mechanical motion. If LCP 100 is still securely attached to the heart wall, the orientation with respect to gravity will remain similar to a previous measurement, such as the most recent measurement or a template measurement. If LCP 100 becomes dislodged, the orientation with respect to gravity may be different with respect to a previous measurement. For instance, LCP 100 may determine that dislodgment has occurred if the orientation with respect to gravity differs in any axis from a previous measurement by more than a threshold value of about thirty degrees. This is just one example, and it is contemplated that other threshold values may be used, such as about twenty degrees, about twenty-five degrees, about thirty-five degrees, about fifty degrees, about seventy-five degrees, about ninety degrees, about one-hundred five degrees, or any other suitable value. In alternative embodiments, LCP 100 may determine dislodgment has occurred only if one or two axes differ from a previous measurement by a threshold amount.

In still more alternative embodiments, the dislodgment metric may be or include a capture threshold. A capture threshold may represent an amount of energy needed in order for an electrical stimulation pulse to capture the heart. In some embodiments, the capture threshold may refer to a specific voltage, a specific pulse width, or a combination of the two, while in other embodiments the capture threshold may refer to a specific amount of energy. Generally, the capture threshold may be less for electrical stimulation pulses delivered by LCP 100 where LCP 100 is securely attached to a wall of the heart than when LCP 100 is dislodged. Accordingly, analysis of the capture threshold, or determining a change in the capture threshold, may be an indication that dislodgment has occurred.

In these embodiments, LCP 100 may determine a baseline capture threshold while LCP 100 is securely attached to a wall of the heart. LCP 100 may then periodically determine the capture threshold, for example about once every hour, about once a day, about once a week, or any other suitable time period. LCP 100 may then determine a correlation parameter based on the current capture threshold and the baseline capture threshold. For instance, LCP 100 may determine a correlation parameter in any manner similar to that described with respect to FIGS. 9-12. LCP 100 may then compare the correlation parameter to one or more thresholds and determine a dislodgment status based on the comparison, again in any manner similar to that described with respect to FIGS. 9-12.

Instead of relying on a single dislodgment metric, LCP 100 may employ multiple dislodgment metrics in determining whether dislodgment has occurred. For instance, when in a dislodgment mode, LCP 100 may be configured to monitor any combination of the described dislodgment metrics, ranging from any combination of two of the dislodgment metrics to all of the dislodgment metrics. In some of these embodiments, LCP 100 may determine that dislodgment has occurred if any one of the monitored dislodgment metrics indicates that dislodgment has occurred. In other embodiments, LCP 100 may determine that dislodgment has occurred only if multiple of the monitored dislodgment metrics indicate that dislodgment has occurred. In still other embodiments, LCP 100 may determine that dislodgment has occurred only if all monitored dislodgment metrics indicate that dislodgment has occurred.

In still other embodiments, LCP 100 may monitor multiple dislodgment metrics in a cascading fashion. For instance, LCP 100 may initially only monitor a first dislodgment metric. After the first dislodgment metric indicates that dislodgment has occurred, LCP 100 may then begin to monitor a second dislodgment metric. In these embodiments, only once the second dislodgment metric has indicated that dislodgment has occurred may LCP 100 determine that dislodgment has occurred. In these embodiments, LCP 100 may be able to cascade the monitored dislodgment metrics in order to save energy. For instance, in some embodiments LCP 100 may be configured to monitor cardiac electrical signals for therapy delivery purposes. For example, monitoring cardiac electrical signals for determining a dislodgment status may not require substantial additional power. Accordingly, a first monitored dislodgment metric may be cardiac electrical signals. Only after the cardiac electrical signals indicate that dislodgment has occurred will LCP 100 begin to monitor a second dislodgment metric, such as accelerometer signals, temperature, impedance, capture threshold, device orientation or the like. If analysis of the second dislodgment metric also indicates that dislodgment has occurred, LCP 100 may then determine that dislodgment has occurred and generate an alarm signal. In different embodiments, LCP 100 may use any of the above described dislodgment metrics in any cascading combination in order to determine whether dislodgment has occurred.

In some embodiments, analysis of a dislodgment metric may differ depending on whether the dislodgment metric is a first dislodgment metric or a second dislodgment metric. As one example, as described above, if the capture threshold is used as a dislodgment metric, LCP 100 may periodically determine the capture threshold and compare the determined capture threshold to a baseline capture threshold to determine whether dislodgment has occurred. However, where the capture threshold is a second dislodgment metric, LCP 100 may simply determine whether the dislodgment metric has changed. For instance, LCP 100 may deliver an electrical stimulation pulse to the heart with a characteristic or characteristics (e.g. voltage, pulse width, or total energy) that are twice the capture threshold. If the delivered electrical stimulation pulse does not capture the heart, LCP 100 may confirm the analysis of the first dislodgment metric that dislodgment has occurred. It should be understood that this is only one example of how analysis of a dislodgment metric may differ depending on whether the dislodgment metric is a first dislodgment metric or a second dislodgment metric. Where other dislodgment metrics are used as second dislodgment metrics, the value of those dislodgment metrics may simply be, for example, compared to a threshold instead of having the LCP 100 determine one or more correlation metrics for comparison to one or more thresholds.

After determining that dislodgment has occurred, LCP 100 may generate an alarm signal and communicate the alarm signal to a device external to LCP 100. For instance, where LCP 100 is part of a medical device system, such as system 400, LCP 100 may communicate the alarm signal to external support device 420. External support device 420 may then generate a visual or audible alarm to notify a user in the vicinity of external support device 420 that LCP 100 has determined that dislodgment has occurred. In other embodiments, LCP 100 may communicate the alarm signal to another internally implanted device, for instance pulse generator 406, and the other internally implanted device may communicate the alarm signal to a device outside of the patient. In some embodiments, LCP 100, or another device which receives the alarm signal from LCP 100, may be connected to one or more wireless networks. LCP 100, or another device of the system, may connect to the wireless network to communicate the alarm signal to a remote device, such as a pager, cell phone, or other remote device connected to the wireless network.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A method for determining a dislodgement status of an implantable device at an implant site on the heart of a patient, the implantable device having an accelerometer for providing an accelerometer signal, the method comprising:
   collecting, by the implantable device operating in a first operating mode, a first number of discrete accelerometer signal samples during a first portion of a cardiac cycle of the heart and using the first number of discrete accelerometer signal samples to determine a first patient parameter, wherein the first portion of the cardiac cycle beginning after a repolarization of the heart during the cardiac cycle and ending before a subsequent polarization of the heart;
   collecting, by the implantable device operating in a second operating mode, a second number of discrete accelerometer signal samples during a second portion of a cardiac cycle of the heart and using the second number of discrete accelerometer signal samples to determine a dislodgment status of the implantable device, wherein the second portion of the cardiac cycle including at least part of a polarization of the heart during the cardiac cycle, wherein the first number is smaller than the second number; and
   providing a notification of the dislodgment status to a remote device that is remote from the implantable medical device.

2. The method of claim 1, wherein the implantable device is a leadless cardiac pacemaker.

3. The method of claim 1, wherein the first patient parameter is used by the implantable device to affect a therapy delivered by the implantable device.

4. The method of claim 1, wherein the first patient parameter comprises one of:
   a posture; and
   an activity level.

5. The method of claim 1, wherein the first patient parameter represents an activity level of the patient, and is used by the implantable device to affect a pacing rate of a pacing therapy delivered by the implantable device to the heart of the patient.

6. The method of claim 1, wherein the implantable device collects the discrete accelerometer signal samples by selectively turning on and off the accelerometer of the implantable device.

7. The method of claim 1, wherein the first portion and the second portion are of the same cardiac cycle.

8. The method of claim 7, wherein the first portion and the second portion are of different cardiac cycles.

9. A leadless cardiac pacemaker (LCP) comprising:
   a plurality of electrodes;
   an accelerometer; and
   a controller operatively coupled to the plurality of electrodes and the accelerometer, the controller configured to:
      determine a patient parameter based at least in part on a first amount of accelerometer data collected during a first portion of a cardiac cycle that does not include a contraction of a heart;
      determine a dislodgment status of the leadless cardiac pacemaker based at least in part on a second amount of accelerometer data collected during a second portion of a cardiac cycle that includes at least part of a contraction of the heart, wherein the first amount of accelerometer data is less than the second amount of accelerometer data; and
      communicate the dislodgment status to a remote device that is remote from the leadless cardiac pacemaker.

10. The LCP of claim 9, wherein the first amount of accelerometer data and the second amount of accelerometer data are collected during the same cardiac cycle.

11. The LCP of claim 9, wherein the patient parameter is used by the leadless cardiac pacemaker to affect a therapy delivered by the leadless cardiac pacemaker.

12. The LCP of claim 9, wherein the patient parameter comprises one of:
   a posture; and
   a patient activity level.

13. The LCP of claim 9, wherein a beginning of the first portion of the cardiac cycle and a beginning of the second portion of the cardiac cycle are offset by different amounts relative to a common detected R-wave.

14. A method comprising:
   detecting, by a leadless cardiac pacemaker (LCP) having an accelerometer, an occurrence of a cardiac electrical event;
   collecting, by the LCP, accelerometer signal data during a first time period of a cardiac cycle, wherein the first time period begins a first predetermined amount of time after the detected cardiac electrical event and wherein the first time period does not include a contraction of a heart;
   collecting, by the LCP, accelerometer signal data during a second time period of a cardiac cycle, wherein the second time period begins a second predetermined amount of time after the detected cardiac electrical event and wherein the second time period does include at least part of the contraction of the heart; and
   determining, by the LCP, a dislodgment status of the LCP based at least in part on the accelerometer signal data collected during the second time period.

15. The method of claim 14, wherein the cardiac electrical event an R-wave.

16. The method of claim 15, wherein the first time period begins between 300 ms and 800 ms after the detected R-wave.

17. The method of claim 16, wherein the second time period begins between 0 ms and 50 ms after the detected R-wave.

18. The method of claim 14, wherein the first time period and the second time period are of different cardiac cycles.

* * * * *